United States Patent [19]
Modak et al.

[11] Patent Number: 5,985,918
[45] Date of Patent: *Nov. 16, 1999

[54] ZINC-BASED ANTIIRRITANT CREAMS

[75] Inventors: Shanta Modak, Riveredge, N.J.; Lester Sampath, Nyack; Lauserpina Caraos, Hollis, both of N.Y.

[73] Assignee: The Trustees of Columbia University in the City of New York, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/760,054

[22] Filed: Dec. 4, 1996

[51] Int. Cl.$^6$ .................. A61K 31/315; A61K 31/19; A61K 31/20

[52] U.S. Cl. .................. 514/494; 514/557; 514/558; 514/560; 514/568; 514/886; 514/887

[58] Field of Search ...................... 514/494, 557, 514/558, 568, 560, 887, 886

[56] References Cited

U.S. PATENT DOCUMENTS

| | | | |
|---|---|---|---|
| 3,960,745 | 6/1976 | Billany et al. | 510/132 |
| 4,587,266 | 5/1986 | Verdicchio et al. | 514/635 |
| 4,853,978 | 8/1989 | Stockum | 2/167 |
| 4,889,844 | 12/1989 | Silvetti, Sr. et al. | 514/60 |
| 5,031,245 | 7/1991 | Milner et al. | 2/168 |
| 5,059,416 | 10/1991 | Cherukuri et al. | 514/974 |
| 5,089,205 | 2/1992 | Huang et al. | 264/255 |
| 5,133,090 | 7/1992 | Modak et al. | 604/292 |
| 5,164,107 | 11/1992 | Khan et al. | 252/106 |
| 5,357,636 | 10/1994 | Dresdner, Jr. et al. | 2/161.7 |

FOREIGN PATENT DOCUMENTS

| | | |
|---|---|---|
| 9318745 | 9/1993 | WIPO. |
| 9318852 | 9/1993 | WIPO. |
| 9526134 | 10/1995 | WIPO. |

OTHER PUBLICATIONS

Lawrence, J.C. et al., Evaluation of Phenoxeotol–Chlorhexidine Cream as a Prophylactic Antibacterial Agent in Burns, The Lancet pp. 1037–1040, May 8, 1992.

Fitzgerald et al., Mechanism of Action of Chlorhexidine Diacitate and Phenoxyethanol Singly and in Combination Against Gram–negative Bacteria, 215 Microbic 70:215–229 (1992).

Modak et al., Rapid Inactivation of Infections Pathogens by Chlorhexidine Coated Gloves, Infection control and Hospital Epidemiology, 13:463–47 (1992).

Drug Information for the Health Care Professional, vol. 1A,. USP–D1 1989 Ninth Edition, pp. 792–793, Banta Company, VIR.

PDR—39th Edition, 1985, pp. 2037–2038, Chlorhexidine.

PDR—39th Edition, 1985, p. 1858 Lotrisone.

Schmolka, I.R., The Synergistic Effects of Nonionic Surfactants Upon Cationic Germicidal Agents, J. Soc. Cosmet. Chem., 24:577–592 (1973).

Goodman, Gillman's The Pharmacological Basis of Therapeutics, A Textbook of Pharmacology, Toxicology and Therapeutics for Physicians and Medical Students, Fourth Edition, p. 989 and Table of Contents, The Macmillan Col., 1970.

Heard et al., The Colloidal Properties of Chlorhexidine and its Interaction with Some Macromolecules, J. Pharm. Pharmac. 20:505–12 (1968).

Rubbo et al., A Review of Sterilization and Disinfection, Year Book Medical Publishers, Chicago, 161–162 (1965).

*Primary Examiner*—John Pak
*Attorney, Agent, or Firm*—Baker & Botts LLP

[57] ABSTRACT

The present invention relates to the use of organic salts of zinc in topical formulations. Such organic salts tend to be less water soluble and therefore less likely to result in systemic toxicity, even with chronic use. In preferred embodiments, the composition of the invention comprise zinc salicylate, which provides the antiinflammatory effect of salicylate, but wherein the zinc moiety counteracts toxic effects associated with salicylate.

7 Claims, No Drawings

ZINC-BASED ANTIIRRITANT CREAMS

1. INTRODUCTION

The present invention relates to hydrophilic and hydrophobic creams which comprise 0.1–15 percent by weight of an organic salt of zinc as an antiirritant, and to the use of such creams in methods of preventing skin irritation. In preferred embodiments, the cream comprises zinc salicylate, which may be present in combination with another zinc salt.

2. BACKGROUND OF THE INVENTION

Local skin reactions such as itching, redness and welts may occur when certain individuals who are allergic come in contact with irritants such as perfumes, cosmetics, sunscreens, aerosols, plant products (e.g. poison ivy and poison oak), and latex medical gloves. Topical formulations containing antihistamines and/or corticosteroids are routinely used to treat such allergic reactions, but are not recommended for chronic use and may, themselves, lead to sensitivity reactions.

Several zinc compounds have been used in topical skin formulations, but the results have not, hitherto, been satisfactory. For example, creams containing zinc oxide at high concentrations (20–40 percent by weight) have been used as skin protectants, but tend to create a thick coating which is not readily washable and which is, therefore, uncomfortable to the skin.

Further, compositions containing readily soluble zinc acetate (at 1–2 percent by weight), combined with antihistamine, have been used to prevent local itching when used topically (e.g. "Benadryl Itch Stopping Cream", Warner Wellcome). However, chronic use of such soluble zinc compounds may potentially result in systemic toxicity. Zinc salts have also been used to block adhesion of anti-irritant compounds to the skin, as set forth in PCT/US95/03744, and zinc gluconate gels have been found to exert a soothing effect.

3. SUMMARY OF THE INVENTION

The present invention relates to the use of organic salts of zinc in topical formulations. Such organic salts tend to be less water soluble than inorganic zinc salts, and are therefore less likely to result in systemic toxicity, even with chronic use. In preferred embodiments, the compositions of the invention comprise zinc salicylate, which provides the anti-inflammatory effect of salicylate, but wherein the zinc moiety counteracts toxic effects associated with salicylate.

4. DETAILED DESCRIPTION OF THE INVENTION

The present invention relates to compositions and methods whereby organic salts of zinc are used in anti-irritant creams for topical application.

Organic salts of zinc which may be used according to the invention include, but are not limited to, zinc salicylate, zinc tannate, zinc gluconate, zinc undecylenate, zinc valerate, zinc laureate, zinc stearate, zinc caproate, zinc gallate, zinc lactate, zinc myristate, zinc palmitate, and zinc propionate. In particular embodiments, the present invention relates to the use of zinc salts of organic acids with a higher number of carbon atoms (6 and above). Unlike readily soluble zinc salts which have a higher rate of ionization (e.g. zinc acetate, zinc sulfate, zinc carbonate etc.), the zinc salts of organic acids containing 6 or more carbons exhibit a low rate of ionization of zinc. These salts act as anti-irritants by a dual mode of action: (1) they provide sustained low levels of zinc ions on the skin surface which can inactivate existing and invading irritants; and (2) because of its low ionization property, the zinc stabilizes the anionic moiety of the salts and prolongs their retention on the skin surface where they form a barrier matrix. This matrix prevents the irritant from contacting the skin surface.

The organic salts of zinc may be comprised in a cream base which may be hydrophilic or hydrophobic. Suitable cream bases include, for example and not by way of limitation, Cetaphil cream (obtainable from Galderma Laboratories, Inc., Fort Worth, Tex.), "Soft-Sense" (Johnson & Son, Inc., Racine, Wis.), "Lotion Soft" (Calgen Vestal, St. Louis, Mo.), "Curel" (Bausch & Lomb Inc., Rochester, N.Y.), and "Purpose" (Johnson and Johnson,). For example, "Soft-Sense" is known to contain purified water, glycerin USP, distearyldiammonium chloride, petroleum USP, isopropyl palmitate, 1-hexadecanol, tocopherol acetate (vitamin E USP), dimethicone, titanium dioxide USP, methyl paraben, propyl paraben, sodium chloride and fragrance. "Lotion Soft" is known to be a nonionic moisturizing lotion which contains a mucopolysaccharide. "Curel" is known to contain deionized water, glycerine, quaternium-5, petroleum, isopropyl palmitate, 1-hexadecanol, dimethicone, sodium chloride, fragrance, methyl paraben and propyl paraben.

The concentration of organic zinc salt may vary from 0.1–15 percent by weight, and is preferably 1–15 percent by weight. In particular embodiments, the cream may comprise 0.1–1 percent by weight of zinc salicylate, wherein one or more other organic zinc salts may optionally be present. The concentration(s) of organic zinc salt(s) present are therapeutically effective in decreasing or preventing skin irritation in a subject.

Accordingly, preferred, nonlimiting embodiments of the invention provide for topical compositions comprising (a) between about 1 and 15 percent by weight (inclusive of 1 and 15 percent) of an organic zinc salt selected from the group consisting of zinc tannate, zinc undecylenate, zinc valerate, zinc laureate, zinc stearate, zinc caproate, zinc gallate, zinc lactate, zinc myristate, zinc palmitate, zinc gluconate and zinc propionate; and (b) between about 0.1 and 1 percent by weight (inclusive of 0.1 and 1 percent) of zinc salicylate, in a cream base.

The present invention also provides for methods of decreasing and/or preventing irritation of the skin of a human or non-human animal subject in need of such treatment, comprising applying a cream according to the invention to at least a portion of the skin of the subject either prior to, during, or after exposure to an irritant such as an allergen or inflammatory substance. In preferred, nonlimiting embodiments, the cream comprises both zinc salicylate as well as at least one other organic zinc salt.

The following nonlimiting formulations have been found to be effective: 5 percent zinc stearate in Cetaphil cream base; 5 percent zinc salicylate in Cetaphil cream base; and 5 percent zinc undecylenate in Cetaphil cream base. The following formulations have been found to be especially effective: 5 percent zinc palmitate in Cetaphil cream base; 4 percent zinc palmitate+4 percent zinc stearate+1 percent zinc salicylate in Cetaphil cream base; 3 percent zinc stearate+0.5 percent zinc salicylate in Cetaphil; and 5 percent zinc stearate+1 percent zinc salicylate in a hydrophilic cream base. Effective, but less rapidly acting, were: 5 percent zinc lactate in Cetaphil cream and 5 percent zinc acetate in Cetaphil cream.

The methods and compositions of the invention may be used to decrease and/or prevent irritation caused by any substance which may produce visible or invisible (but subjective) irritation in the skin of an individual. The cream of the invention may be applied before, during and/or after exposure. Nonlimiting examples of irritants include: latex or other medical gloves, coated with starch or otherwise; plant substances, such as poison ivy or poison oak; pet allergens, such as dog or cat dander; cosmetics; perfumes; pollen; detergents; disinfectants; soaps; insect bites and stings; coelenterate stings; sunscreens; etc.

5. EXAMPLES

A volunteer who is sensitive to latex-starch gloves tested the following creams before donning the glove. A Placebo cream was used (control) under the glove on one hand and the test cream was used on the other hand. The gloves were worn for three hours if no reaction occurred. If a reaction occurred before three hours, the gloves were removed and the reaction noted. The various zinc salts as shown in Table A were incorporated into Cetaphil Moisturizing Cream (Galderma) and used for the test. Results are shown in Table A.

TABLE A

Effect of Topical Creams Containing Organic Zinc Salts on Preventing Skin Reaction from Contact with Latex Starch Gloves

| % Zinc salts in cream | % zinc in cream | Reactions |
| --- | --- | --- |
| 2% Zinc salicylate | 0.38 | Itching, redness after 30' |
| 4% Zinc salicylate* | 0.76 | No reaction for >3 hours |
| 5% zinc acetate | 1.8 | No reaction for >3 hours |
| 2% zinc acetate | 0.7 | Itching, redness after 30' |
| 5% zinc lactate | 1.4 | No reaction for >3 hours |
| 2.5% zinc lactate | 0.7 | Slight itching after 1 hour |
| 5% zinc undecylenate | 0.7 | Itching after 1 hour |
| 5% zinc gluconate | 0.7 | No reaction for >3 hours |
| 5% zinc stearate | 0.5 | No reaction for >3 hours |
| 10% zinc gluconate* | 1.4 | No reaction for >3 hours |
| 2.5% zinc stearate | 0.25 | Itching after 1 hour |
| 2.5% zinc stearate +* 1% zinc salicylate | 0.25+ 0.19 | No reaction for >3 hours |
| 2.5% zinc stearate + 1% zinc acetate | 0.25+ 0.35 | Itching after 1 hour |
| 5% zinc stearate +* 1% zinc salicylate | 0.5 0.19 | No reaction for >3 hours |
| placebo cream | — | Itching, Redness after 15 minutes |

All the zinc salts were incorporated in Cetaphil Moisturizing Cream.
*These creams provided increased comfort and good after feel on the hand.

Soluble and sparingly soluble zinc salts such as zinc acetate and zinc lactate were effective at higher zinc concentrations (1.4% Zn and 1.8% Zinc respectively). However sparingly soluble zinc salicylate or zinc gluconate were effective at lower concentrations (0.7% zinc). The insoluble zinc stearate was effective at a zinc concentrations of 0.5%.

It appears from the results that the acid moiety of the zinc salts also contribute to the anti-irritant effect. The stearate, salicylate and gluconate molecule form a protective barrier either in the form of a gel or a film matrix when topical compositions containing these compounds are applied on the hand thus preventing the irritants from contacting the skin. In addition small amounts of zinc from these compounds (especially zinc gluconate and zinc stearate) stay on the surface of the skin and inactivate the irritants.

The results in Table A also show that when lower amounts of zinc salicylate and zinc stearate are used in combination, they are as effective as the single compounds at higher concentrations. Moreover, addition of small amounts of zinc salicylate to either zinc gluconate or zinc stearate improves the texture of the cream, feel on the hand and relieves pain.

Evaluation of the anti-irritant effect of different zinc salts show that zinc salts of (1) long chain (e.g., greater than or equal to 6 carbons) acids such as zinc gluconate (2) higher fatty acids such as zinc palmitate, zinc stearate etc., (3) aromatic acids such as zinc salicylate are highly effective as anti-irritants. Sparingly soluble or insoluble salts when used either alone or in combination appear to provide better barrier effect than soluble zinc salts. They can be used either alone or in combination.

Topical compositions containing the following zinc salts can be prepared either in a hydrophilic or hydrophobic base which forms a gel or film matrix when applied on the skin surface.

TABLE B

Compounds in the Cream Base

| | |
| --- | --- |
| A | Zinc gluconate - 9% |
| B | zinc stearate - 9% |
| C | Zinc salicylate - 4% |
| D | zinc gluconate + zinc salicylate 5% + 1% |
| E | Zinc stearate + Zinc salicylate – 2.5% + 1% |
| F | Zinc stearate + Zinc salicylate – 5% + 1% |
| G | Zinc gluconate + Zinc stearate + Zinc salicylate – 0.5% + 2.5% + 0.5% |

Compositions A, F and G in a hydrophilic cream base were tested on volunteers for the following symptoms.

TABLE C

| | A | F | G |
| --- | --- | --- | --- |
| Insect Bite | effective | effective | effective |
| Prickly Heat | effective | effective | effective |
| Metal Sensitivity | effective | effective | effective |
| Plant Irritants | effective | effective | effective |

F and G were more effective. The burn and itching disappeared faster (within 5') when these creams were applied. In the case of cream A the symptoms disappeared in 10–20'.

TABLE D

Comparisons of the following creams with regard to comfort on the Hand When Used Under the Glove and Feel After Washing the Cream Off

| | Comfort on the hand Volunteer | | After feel Volunteer | |
| --- | --- | --- | --- | --- |
| zinc salt in cream | 1 | 2 | 1 | 2 |
| A Zn Gl 9% | Good | Good | Good | Good |
| F Zn st + Zn sal 5% + 1% | Good | Good | Good | Good |
| G Zn Gl + Zn st + Zn sal 5% + 2.5% + 0.5% + 0.5% | Excellent | Excellent | Good | Good |

Zn st = Zinc stearate
Zn Gl = Zinc gluconate
Zn sal = Zinc salicylate

Various publications are cited herein which are hereby incorporated by reference in their entireties.

What is claimed is:

1. A topical composition comprising:
   (a) between about 1 and 15 percent by weight of zinc stearate; and
   (b) between about 0.1 and 1 percent by weight of zinc salicylate;
   in a topical cream base.

2. The composition of claim 1 wherein the topical cream base is hydrophobic.

3. The composition of claim 1 wherein the topical cream base is hydrophilic.

4. A method for decreasing irritation of the skin of a subject comprising applying a therapeutically effective amount of an antiirritant cream to at least a portion of the skin of the subject, wherein the antiirritant cream comprises
   (a) between about 1 and 15 percent by weight of zinc stearate; and
   (b) between about 0.1 and 1 percent by weight of zinc salicylate;
   in a topical cream base.

5. The method of claim 4, wherein the antiirritant cream is applied prior to exposure to an irritant.

6. The method of claim 4, wherein the antiirritant cream is applied during exposure to an irritant.

7. The method of claim 4, wherein the anfiirritant cream is applied after exposure to an irritant.

* * * * *